US012564361B2

(12) United States Patent
Shin et al.

(10) Patent No.: US 12,564,361 B2
(45) Date of Patent: Mar. 3, 2026

(54) RADIOGRAPHIC DEVICE AND RADIATION FLUX CONTROL METHOD

(71) Applicant: DRTECH CORPORATION, Seongnam-si (KR)

(72) Inventors: Choul Woo Shin, Seongnam-si (KR); Chang Gyu Lee, Yongin-si (KR); Jong Woo Kim, Yongin-si (KR); Cheon Kyung Sung, Uijeongbu-si (KR); Jeon Min Kang, Seongnam-si (KR)

(73) Assignee: DRTECH CORPORATION, Seongnam-si (KR)

( * ) Notice: Subject to any disclaimer, the term of this patent is extended or adjusted under 35 U.S.C. 154(b) by 295 days.

(21) Appl. No.: 18/269,328

(22) PCT Filed: Dec. 24, 2021

(86) PCT No.: PCT/KR2021/019892
§ 371 (c)(1),
(2) Date: Jul. 18, 2023

(87) PCT Pub. No.: WO2022/139561
PCT Pub. Date: Jun. 30, 2022

(65) Prior Publication Data
US 2024/0057952 A1 Feb. 22, 2024

(30) Foreign Application Priority Data

Dec. 24, 2020 (KR) ........................ 10-2020-0183468
Dec. 23, 2021 (KR) ........................ 10-2021-0186523

(51) Int. Cl.
A61B 6/06 (2006.01)
A61B 6/00 (2024.01)
A61B 6/46 (2024.01)

(52) U.S. Cl.
CPC ................ *A61B 6/06* (2013.01); *A61B 6/465* (2013.01); *A61B 6/542* (2013.01)

(58) Field of Classification Search
CPC ........... A61B 6/06; A61B 6/469; A61B 6/465; A61B 6/542
See application file for complete search history.

(56) References Cited

U.S. PATENT DOCUMENTS 7,206,383 B2 * 4/2007 Zhao ........................ G21K 1/04
378/150
9,271,687 B2 * 3/2016 Koh ........................ A61B 6/469
(Continued)

FOREIGN PATENT DOCUMENTS

KR 1020130097129 A 9/2013
KR 1020140017339 A 2/2014
(Continued)

OTHER PUBLICATIONS

Translated KR20190141117 (Year: 2019).*
Office Action of KR Patent Application No. 10-2021-0186523 dated Nov. 2, 2023.

*Primary Examiner* — David J Makiya
*Assistant Examiner* — Soorena Kefayati
(74) *Attorney, Agent, or Firm* — Dinsmore & Shohl LLP; Yongsok Choi, Esq.

(57) ABSTRACT

A radiographic device includes an radiation irradiator which can irradiate a subject with radiation, and which includes a collimator capable of selectively blocking radiation flux; an image acquisition unit for acquiring an image signal by receiving the radiation that has passed through the subject; a display unit for displaying a radiation image on the basis of the image signal; and a determination controller which can control the irradiation unit so that the irradiation range (Continued)

of the radiation corresponding to a selection area selected from the radiation image is implemented.

6 Claims, 7 Drawing Sheets

(56)                    References Cited

U.S. PATENT DOCUMENTS

| | | | | |
|---|---|---|---|---|
| 2011/0274240 | A1* | 11/2011 | Sugaya | A61B 6/405 |
| | | | | 378/16 |
| 2013/0077745 | A1* | 3/2013 | Wang | A61B 6/06 |
| | | | | 378/62 |
| 2013/0163721 | A1* | 6/2013 | Koh | A61B 6/06 |
| | | | | 378/62 |
| 2013/0336445 | A1* | 12/2013 | Sehnert | G01N 23/044 |
| | | | | 378/42 |
| 2014/0037057 | A1* | 2/2014 | Kim | A61B 6/469 |
| | | | | 378/98.2 |
| 2015/0110245 | A1* | 4/2015 | Kim | A61B 6/488 |
| | | | | 378/62 |
| 2015/0265226 | A1* | 9/2015 | Jackson | A61B 6/032 |
| | | | | 378/16 |
| 2015/0297159 | A1* | 10/2015 | Melman | A61B 6/467 |
| | | | | 378/62 |
| 2015/0327821 | A1* | 11/2015 | Hu | A61B 6/544 |
| | | | | 378/62 |
| 2016/0058403 | A1* | 3/2016 | Kim | A61B 6/467 |
| | | | | 378/98.2 |
| 2016/0317104 | A1* | 11/2016 | Guez | A61B 6/4441 |
| 2017/0020469 | A1* | 1/2017 | Lee | A61B 6/4417 |
| 2018/0028138 | A1* | 2/2018 | Oh | A61B 6/5235 |
| 2019/0343479 | A1* | 11/2019 | Sato | A61B 6/06 |
| 2020/0229783 | A1* | 7/2020 | Jung | A61B 6/025 |
| 2020/0312478 | A1* | 10/2020 | Sutter | A61B 6/06 |

FOREIGN PATENT DOCUMENTS

| | | | | |
|---|---|---|---|---|
| KR | 101501086 | B1 | 3/2015 | |
| KR | 20190141117 | A | * 12/2019 | A61B 6/465 |

* cited by examiner

FIG. 1

110 — RADIATION IRRADIATOR

IMAGE ACQUISITION UNIT — 120

DETERMINATION CONTROLLER

DISPLAY UNIT — 140

130

(a)

140        405        407

(b)

140

RADIOGRAPHIC DEVICE AND RADIATION FLUX CONTROL METHOD

CROSS-REFERENCE TO RELATED APPLICATIONS

This application is a national phase of International Application No. PCT/KR2021/019892 filed on Dec. 24, 2021, which claims priority to Korean Patent Application No. 10-2020-0183468 filed on Dec. 24, 2020 and Korean Patent Application No. 10-2021-0186523 filed on Dec. 23, 2021, the entire contents of which are herein incorporated by reference.

TECHNICAL FIELD

The present invention relates to a radiographic device and a radiographic method using the same.

BACKGROUND ART

Radiographic devices using radiation such as X-rays are imaging devices that radiate radiation onto an affected part of a human or animal body and receive penetrating radiation to acquire an image of the affected part. Such radiographic devices are devices that continuously or consecutively provide radiographic images of an affected part and are widely used for diagnosing or reading of the affected part and various medical procedures.

Since a radiographic device radiates radiation such as X-rays onto a subject, it is important to control a radiation dose applied to the subject. In particular, since a C-arm type radiographic device performs X-ray imaging for a relatively long time, it is necessary to minimize an X-ray dose. In addition, recently, a need for precise high-resolution and real-time images for accurate diagnosis and treatment has increased considerably, and in order to improve the quality of a radiographic image, an increase in radiation dose is also necessary.

In particular, recently in the medical imaging field, a need for precise high-resolution and real-time images for accurate diagnosis and treatment has been considerably increasing. For example, imaging devices such as a C arm type fluoroscopy device providing real-time images, a high-definition X-ray imaging device, and a CT device providing various tomographic images and three dimensional (3D) reconstruction images are being developed. Interventional procedures using 3D imaging (CT) and fluoroscopy are increasing. In this case, the quality of X-ray images should be excellent to increase the stability of the surgery procedure, and a radiation dose is inevitably increased to obtain a high-quality image. For this reason, it is important to control an X-ray exposure dose in a radiographic device, particularly in a C arm X-ray imaging device.

In conventional radiographic devices, a collimator is provided to adjust a flux of radiation. Two leaf collimators may be moved at both sides with respect to a center of a flux of radiation to block a flux portion of radiation.

When an image biased to one side from the center of a radiographic image or an area of interest is positioned at a periphery rather than the center of the radiographic image, there has been a problem of unnecessary radiation exposure to parts other than the area of interest, and in some cases, there has also been a problem that a radiation dose has been increased because a radiation irradiator should be repositioned to perform imaging again to adjust the brightness of radiation. In addition, when a position of a collimator needs to be reset due to the patient's movement after the position of the collimator is set, there has been a problem that both a patient and a photographer have been exposed to additional radiation.

RELATED ART DOCUMENTS

Patent Documents

Patent Document 1) Korean Patent Registration No. 10-1501086 (Mar. 4, 2015).

DISCLOSURE

Technical Problem

The present invention is directed to providing a radiographic device capable of reducing a radiation exposure dose to a user by performing local radiography on a selection area in a radiographic image, and a radiation flux control method using the same.

Technical Solution

According to an embodiment of the present invention, a radiographic device includes an radiation irradiator configured to radiate radiation onto an irradiation target object and including a collimator configured to selectively block a flux of the radiation, an image acquisition unit configured to acquire an image signal by receiving the radiation penetrating the irradiation target object, a display unit configured to display a radiographic image based on the image signal, and a determination controller configured to control the radiation irradiator such that an irradiation range of the radiation corresponding to a selection area selected in the radiographic image is implemented.

The radiographic device may further include an input unit configured to receive the selection area in the radiographic image from a user.

The display unit may include a touch screen configured to receive the selection area selected in the radiographic image from a user.

The collimator may be provided as a plurality of collimators, and the plurality of collimators may be provided to be simultaneously driven.

The plurality of collimators may move asymmetrically or non-interlockingly with each other to block at least a portion of the flux of the radiation.

In the radiographic image displayed on the display unit, a portion corresponding to the selection area may be enlarged and displayed.

According to another embodiment of the present invention, a radiographic device includes a radiation irradiator configured to radiate radiation and vary an irradiation range of the radiated radiation, an image acquisition unit configured to acquire an image signal by receiving the radiation that is radiated from the radiation irradiator and penetrates an irradiation target object, a display unit configured to display a radiographic image based on the image signal and set a desired selection area in the displayed radiographic image, and a determination controller configured to, when the selection area is set by the display unit, implement an irradiation range of the radiation corresponding to the selection area based on information of the selection area and control the radiation irradiator to radiate the radiation in the implemented irradiation range and acquire an image signal.

The radiation irradiator may include a collimator configured to selectively block a flux of the radiated radiation and adjust the irradiation range of the radiation, and the collimator may operate to implement the irradiation range of the radiation corresponding to the selection area under control of the determination controller.

The display unit may include a touch screen configured to display the radiographic image and receive a touch gesture from a user, and the selection area may be set with the touch gesture input through the touch screen.

The touch gesture may include at least one of a drag touch, a tap touch, a double tap touch, and a press touch.

The selection area may be set through a setting process including a process of setting a basic selection area with a first touch gesture, a process of changing the basic selection area with a second touch gesture to set a changed selection area, and a process of determining the changed selection area as the selection area with a third touch gesture.

The display unit may be configured to display a radiographic image captured in the irradiation range of the radiation corresponding to the selection area through image fitting.

According to still another embodiment of the present invention, a radiation flux control method includes a first image display process of displaying a first radiographic image of an irradiation target object, a selection area setting process of receiving an area selected in the radiographic image to set a selection area, a collimator driving process of blocking a remaining portion excluding a flux portion of radiation corresponding to the selection area using a collimator, and a second image display process of displaying a second radiographic image acquired by radiating the flux portion of the radiation corresponding to the selection area onto the irradiation target object.

In the second image displaying process, the selection area may be enlarged and displayed on the second radiographic image.

According to yet another embodiment of the present invention, a radiographic method includes displaying a first radiographic image of an irradiation target object, receiving an area selected in the radiographic image to set a selection area, at least partially blocking a flux of radiation to radiate radiation having a radiation irradiation range corresponding to the selection area, and displaying a second radiographic image of the irradiation target object acquired by the radiated radiation.

In the radiating of the radiation, the radiation irradiation range corresponding to the selection area may be implemented by adjusting a collimator of a radiation irradiator of a radiographic device.

In the setting of the selection area, the selection area may be set with a touch gesture on the first radiographic image displayed on a touch screen.

In the displaying of the second radiographic image, the second radiographic image may be displayed on a screen of a display unit through image fitting.

Advantageous Effects

According to the present invention, radiation is radiated onto a limited selection area, which is a local area selected by a user, to acquire a radiographic image, thereby reducing a radiation exposure dose. Therefore, when an image is biased to one side from the center of the radiographic image or a user's area of interest is not at the center of the radiographic image and is positioned at an edge, there is an effect of suppressing unnecessary radiation exposure to parts other than the area of interest.

In addition, since surgery can be continued without the movement of a radiation generator during surgery, it is possible to eliminate the inconvenience of having to readjust the position of a radiation irradiator and perform imaging for radiation brightness adjustment again. When a position of a collimator is readjusted, a time taken for adjusting the position of the collimator is shortened, thereby obtaining an effect of shortening a surgery time and improving user convenience.

DESCRIPTION OF DRAWINGS

FIG. 1 is a schematic block diagram illustrating a radiographic device according to an embodiment of the present invention.

MODES OF THE INVENTION

Hereinafter, embodiments of the present invention will be described in detail with reference to the accompanying drawings so that those skilled in the art may easily practice the present invention. However, the present invention may be embodied in various different forms and is not limited to the embodiments to be described hereafter.

Figure 1:
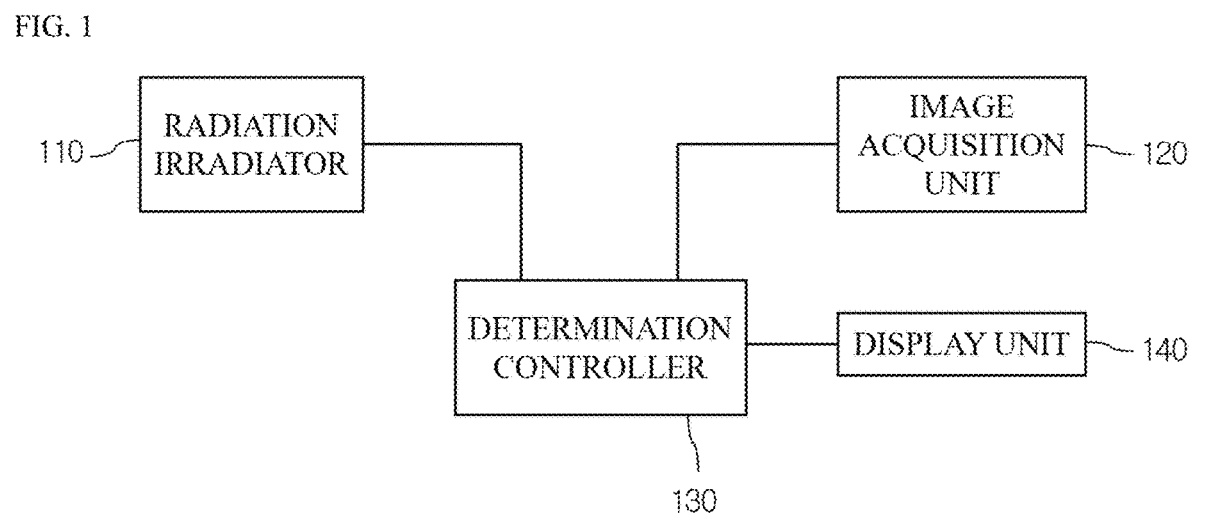

Referring to FIG. 1, a radiographic device according to an embodiment of the present invention includes a radiation irradiator 110, an image acquisition unit 120, a determination controller 130, and a display unit 140. The determination controller 130 may be a processor such as a computer processing unit. The radiation irradiator 110 includes a collimator capable of asymmetrically blocking a flux of radiation in a cross section of the flux of radiation radiated onto an irradiation target object. The collimator may be configured to selectively block the flux of radiation and implement a desired radiation irradiation range. In addition, the radiation irradiator 110 may include a radiation source, for example, an X-ray source for generating radiation, for example, X-rays. The image acquisition unit 120 acquires an image signal by receiving radiation penetrating an irradiation target object. The image acquisition unit 120 may include a radiation detector, for example, an X-ray detector that detects radiation penetrating an irradiation target object, for example, X-rays. The display unit 140 displays a radiological image based on the image signal. The determination controller 130 transmits blocking information, which is for blocking the remaining flux portion of radiation excluding a flux portion of radiation corresponding to a selection area selected in the radiological image, to the radiation irradiator 110.

The radiographic device may further include an input unit that receives a selection area selected in the radiological image from a user.

The display unit 140 may include a touch screen capable of receiving the selection area selected in the radiological image from the user. In this case, an input unit does not need to be provided separately, but even when an input is possible through the display unit 140 such as a touch screen, an input unit such as a mouse, a keyboard, a control panel, or the like may also be provided.

Figure 2:
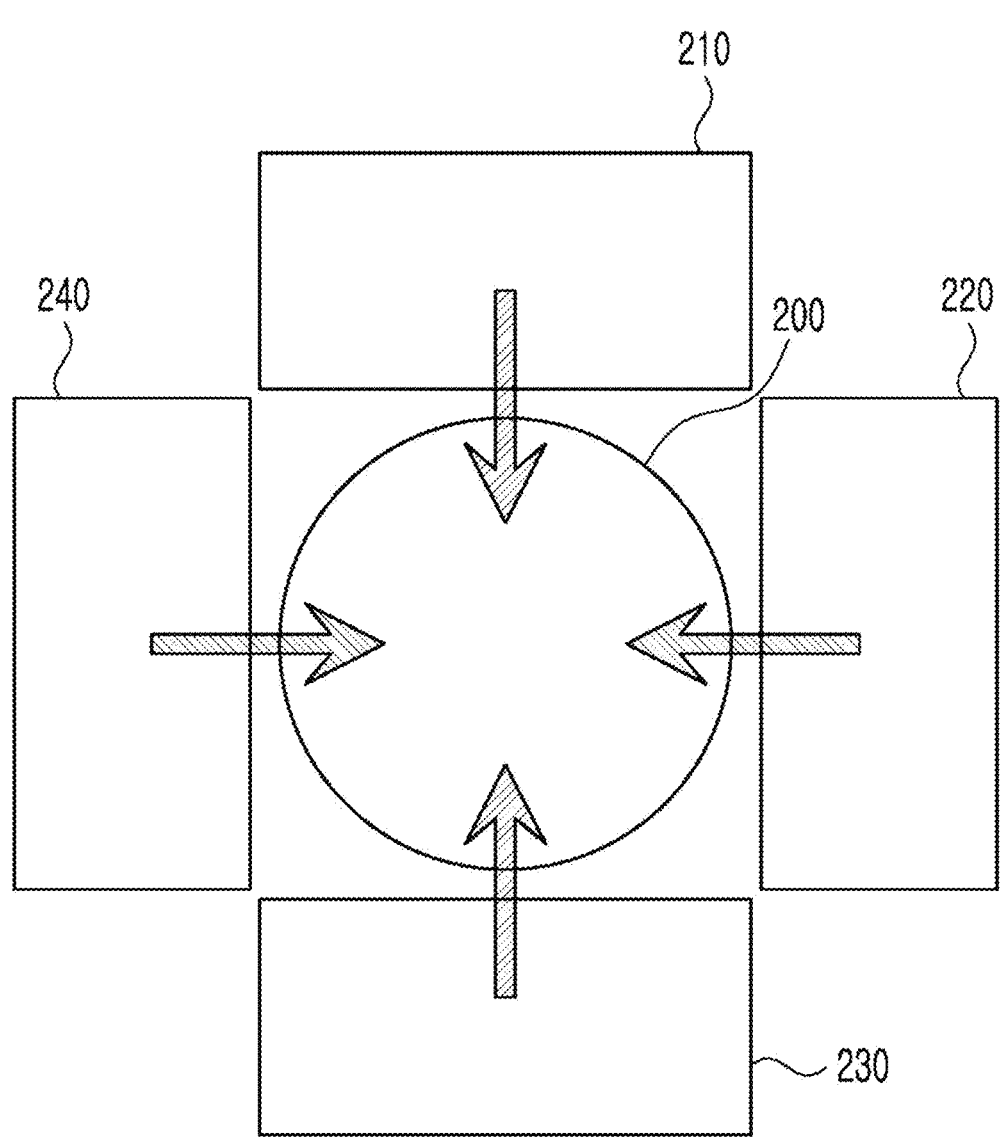
FIGS. 2 and 3 are schematic diagrams illustrating a flux of radiation and a plurality of collimators in a radiation irradiator of the radiographic device according to an embodiment of the present invention.
Figure 3:
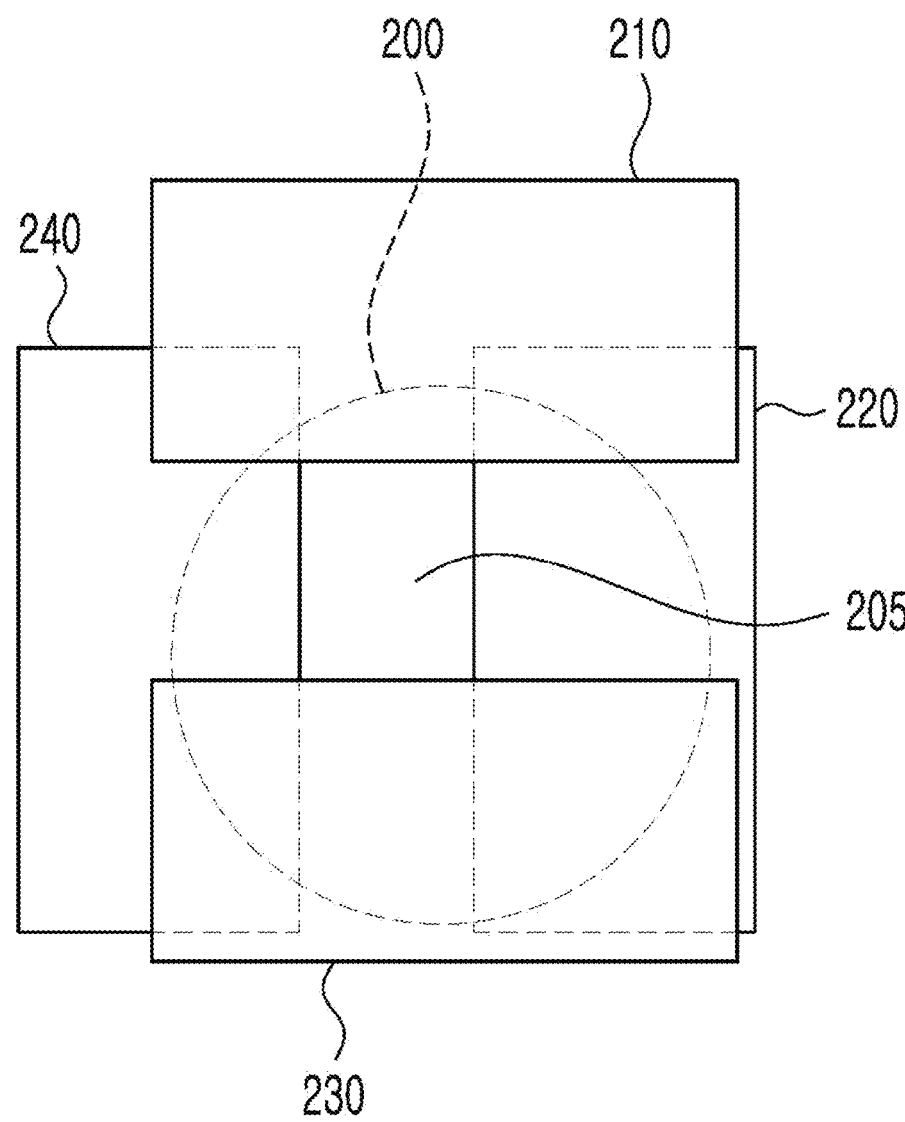

A plurality of collimators 210, 220, 230, and 240 may be provided in the radiation irradiator 110. Preferably, the plurality of collimators 210, 220, 230, and 240 may be simultaneously driven. The collimator provided in the radiation irradiator 110 is not limited to four collimators as shown in FIGS. 2 and 3 and may be implemented in various structures capable of changing or adjusting a radiation irradiation range by at least partially blocking a flux of radiation.

Preferably, the plurality of collimators 210, 220, 230, and 240 are configured to block a portion of a radiation flux 200 by moving asymmetrically or non-interlockingly with each other. In addition, it is also preferable to enlarge and display a portion corresponding to the selection area in the radiological image displayed on the display unit 140.

As an example of the radiation irradiator 110 for radiating radiation onto an irradiation target object, there may be an X-ray generator. In the X-ray generator, an electron beam accelerated from a filament-shaped cathode provided in a vacuum tube is incident on a target material on an anode in a high-energy state to generate X-rays in the form of a conical beam. The radiation irradiator 110 outputs radiation according to a radiation output condition and radiates the radiation onto an irradiation target object. Here, the radiation output condition may include an output voltage and an output current of X-rays which are radiation. The radiation output condition may be received from the determination controller 130.

The determination controller 130 and the radiation irradiator 110 are electrically connected such that the radiation output condition may be transferred from the determination controller 130 to the radiation irradiator 110. Therefore, the radiation irradiator 110 outputs X-rays according to the radiation output condition received from the determination controller 130 and radiates the X-rays onto an irradiation target object. A control signal for controlling the driving of the collimators 210, 220, 230, and 240 may also be transmitted from the determination controller 130 to the radiation irradiator 110. The driving of the collimators 210, 220, 230, and 240 may be controlled according to blocking information which is a control signal for controlling the driving of the collimators 210, 220, 230, and 240.

The collimators 210, 220, 230, and 240 are provided at a front side of the radiation irradiator 110 to determine a shape of X-rays and an irradiation area. The radiation irradiator 110 includes the collimators 210, 220, 230, and 240 capable of asymmetrically blocking a flux of radiation in a cross section of the flux of radiation radiated onto an irradiation target object. The radiation irradiator 110 controls the driving of the collimators 210, 220, 230, and 240 according to a control signal transmitted from the determination controller 130, that is, radiation flux blocking information.

FIGS. 2 and 3 are schematic diagrams illustrating a flux of radiation and the plurality of collimators in the radiation irradiator of the radiographic device according to an embodiment of the present invention. FIG. 2 schematically illustrates a state in which the plurality of collimators do not block a flux of radiation. FIG. 3 schematically illustrates a state in which each of the plurality of collimators blocks a portion of a flux of radiation.

Referring to FIGS. 2 and 3, four collimators 210, 220, 230, and 240 are provided at a front side in a direction in which X-rays, which are radiation, travel from the radiation irradiator 110. Each of the first collimator 210, the second collimator 220, the third collimator 230, and the fourth collimator 240 may move independently toward a center of the radiation flux 200 as indicated by arrows in FIG. 2 according to a control signal, that is, blocking information, thereby blocking a portion of the radiation flux 200 as shown in FIG. 3. That is, each of the first collimator 210, the second collimator 220, the third collimator 230, and the fourth collimator 240 independently moves according to blocking information. In addition, it is preferable that the first collimator 210, the second collimator 220, the third collimator 230, and the fourth collimator 240 move simultaneously. For this, a motor (not shown) may be provided in the radiation irradiator 110 as a driving device for moving the first collimator 210, the second collimator 220, the third collimator 230, and the fourth collimator 240 to block or open a portion of the radiation flux 200.

A portion of the radiation flux 200 not blocked by the first collimator 210, the second collimator 220, the third collimator 230, and the fourth collimator 240 is a portion corresponding to a selection area to be described below and is radiated onto an irradiation target object.

The image acquisition unit 120 acquires an image signal by receiving radiation penetrating an irradiation target object. That is, the image acquisition unit 120 acquires an image signal by converting incident X-rays that have penetrated an irradiation target object into an image signal. The image acquisition unit 120 is positioned opposite to the X-ray generator and converts X-rays penetrating the irradiation target object into a visible light image signal. The image acquisition unit 120 transmits the image signal to the determination controller 130 electrically connected thereto.

The image signal transmitted to the determination controller 130 is transmitted to the display unit 140 and becomes a basis for displaying a radiographic image on the display unit 140. As described above, the display unit 140 displays the radiographic image based on the image signal acquired by the image acquisition unit 120. As an example of the display unit 140 that displays the radiographic image based on the image signal, there may be a display device that visually displays various types of information.

In addition, a form capable of receiving input from a user through a screen, such as a touch screen capable of receiving an input from a user, is also preferable for the display unit 140. The display unit 140 may separately include an input unit such as a mouse as needed. When the display unit 140 has a form capable of receiving an input, such as a touch screen, information input through a touch or a drag by a user's hand or a touch pen may be transmitted to the determination controller 130, and the determination controller 130 may change various settings to reflect the input information.

The determination controller 130 may allow a user to set an irradiation condition or output condition of radiation or may control an X-ray irradiation area by controlling each of the first collimator 210, the second collimator 220, the third collimator 230, and the fourth collimator 240 of the radiation irradiator 110. Also, the determination controller 130 may control the image acquisition unit 120, the radiation irradiator 110, the display unit 140, and the like.

The determination controller 130 transmits blocking information, which is for blocking the remaining portion of a flux of radiation excluding a radiation flux portion 205 corresponding to a selection area selected in a radiological image, to the radiation irradiator 110. In other words, it can be said that the determination controller 130 transmits blocking information for transmitting only the radiation flux portion 205 corresponding to the selection area selected in the radiographic image to the radiation irradiator 110.

Figure 9A:
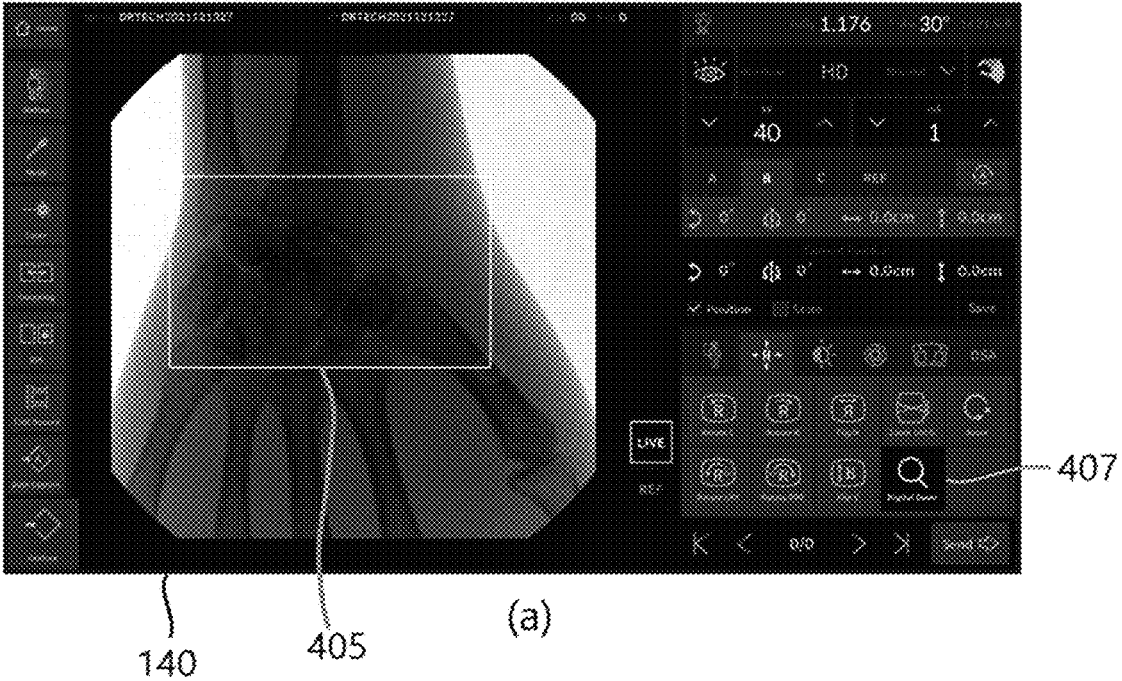
FIG. 9A is an image showing a state in which a selection area is set in an image displayed on a screen of a display unit in the radiographic device according to an embodiment of the present invention.
Figure 9B:
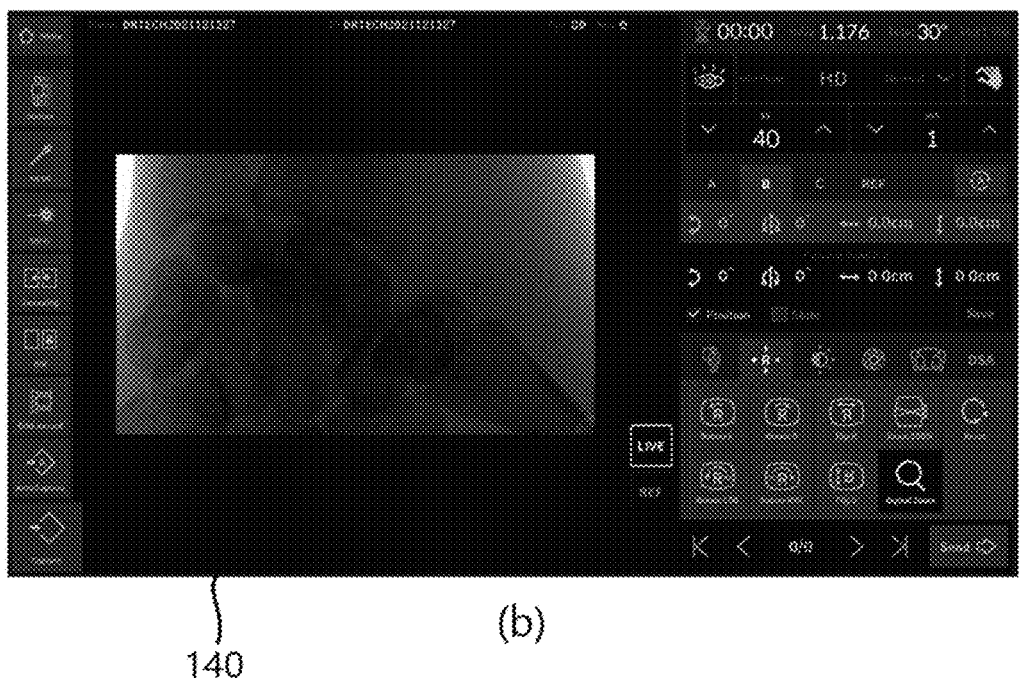
FIG. 9B is an image showing a state in which a radiographic image acquired according to the selection area in FIG. 9A is displayed on the screen of the display unit.

FIG. 9 shows an example in which the radiographic device sets a selection area and displays a radiographic image acquired according to the selection area according to an embodiment of the present invention. First, referring to FIG. 9A, a selection area 405 may be selected in a radiographic image displayed on the screen of the display unit 140, and the selection area 405 may be displayed with a boundary line to be identifiable. When the corresponding selection area is imaged and is to be enlarged in a state in which the selection area 405 is selected, an enlargement command area 407 provided on the display unit 140 is touched to capture an image corresponding to the corresponding selection area. That is, after a position of the collimator is adjusted such that a radiation irradiation range corresponding to the corresponding selection area is implemented, the radiation irradiator 110 is controlled to radiate radiation. As shown in FIG. 9B, a radiographic image newly acquired in this way, that is, an enlarged radiographic image corresponding to the selection area, is displayed on the display unit 140.

The display unit 140 displays a first radiographic image in which a command for selecting the selection area is input and a second radiographic image corresponding to the selection area. To this end, the display unit 140 may separately include an input display which displays the first radiographic image for inputting the selection area and a main display which displays the second radiographic image captured and acquired under conditions corresponding to the selection area. For example, the input display may be provided on a mobile cart of a mobile C arm X-ray device, and the main display may be provided on a separate operating console.

Next, a radiation flux control method using the radiographic device according to an embodiment of the present invention will be described with further reference to FIGS. 4 to 8. The radiographic device according to the embodiment of the present invention may be further understood through the description of the radiation flux control method.

Figure 4:
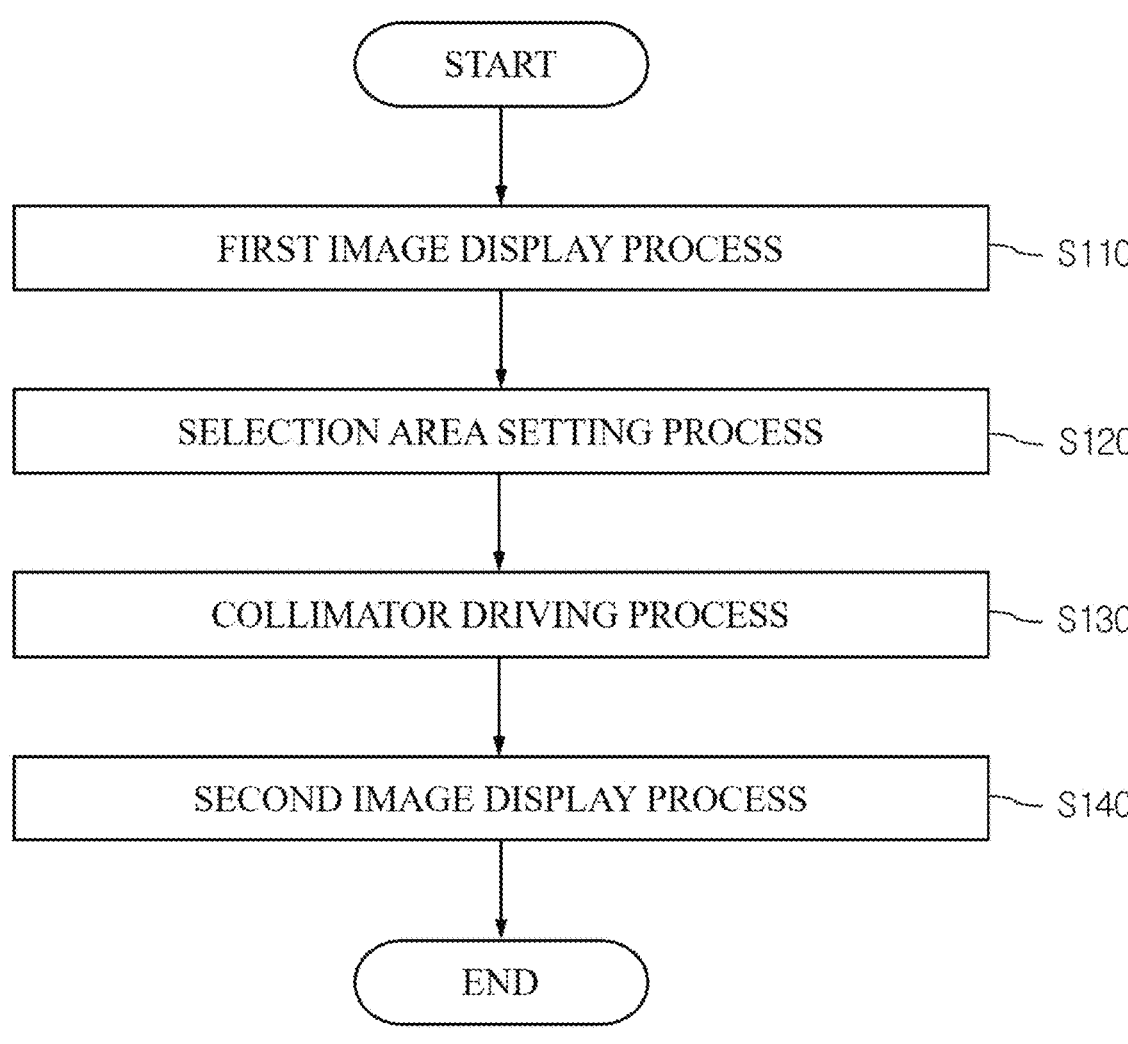
FIG. 4 is a schematic flowchart illustrating a radiation flux control method using the radiographic device according to an embodiment of the present invention.

FIG. 4 is a schematic flowchart illustrating the radiation flux control method using the radiographic device according to the embodiment of the present invention. Referring to FIG. 4, the radiation flux control method using the radiographic device according to the embodiment of the present invention may include the first image display process S110 of displaying a first radiographic image of an irradiation target object, the selection area setting process S120 of receiving an area selected from the radiographic image to set a selection area, the collimator driving process S130 of blocking the remaining portion excluding a portion of a flux of radiation corresponding to the selection area using a collimator, and the second image display process S140 of displaying a second radiographic image acquired by radiating the portion of the flux of radiation corresponding to the selection area onto an irradiation target object.

Here, in the second image display process S140, the portion corresponding to the selection area in the second radiographic image may be enlarged and displayed.

The first image display process S110 is a process of displaying the first radiographic image of the irradiation target object. That is, in the first image display process S110, X-rays which are radiation are radiated onto the irradiation target object, the X-rays penetrating the irradiation target object are received to acquire an image signal, and a radiographic image, that is, an X-ray image, is displayed on the screen based on the image signal such that a user or the like may confirm the acquired image signal.

The radiation irradiator 110 radiates radiation, for example, X-rays, onto the irradiation target object. When the radiation irradiator 110 radiates the X-rays onto the irradiation target object, the X-rays penetrate the irradiation target object and are incident on the image acquisition unit 120.

The image acquisition unit 120 acquires an image signal from the incident X-rays and transmits the acquired image signal to the determination controller 130. The determination controller 130 transmits the image signal to the display unit 140, and the display unit 140 visually displays a radiographic image based on the image signal.

Figure 5:
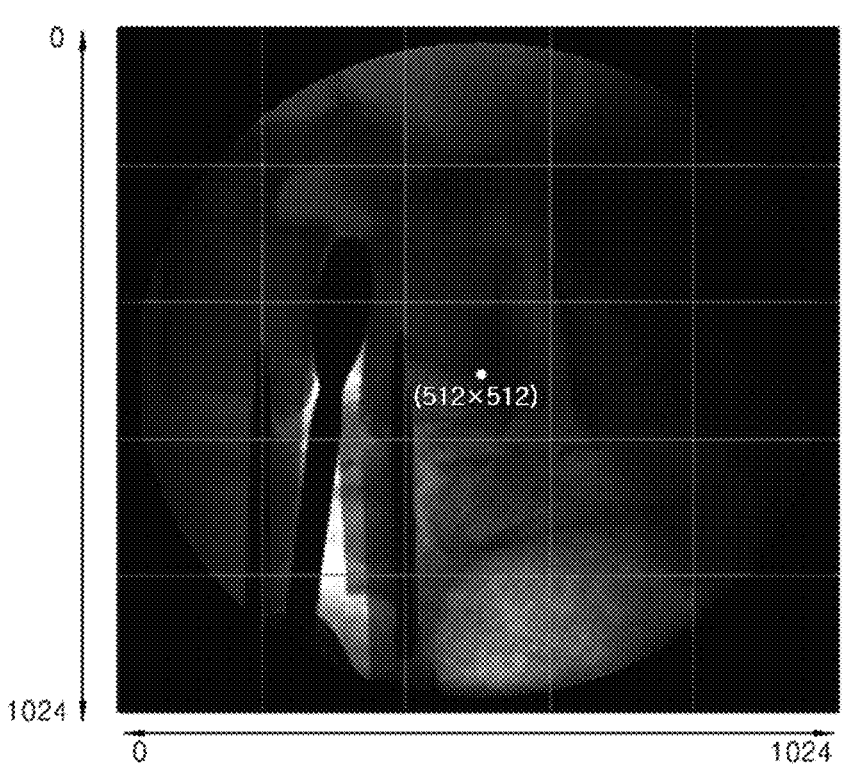
FIG. 5 is a schematic diagram showing an image of a radiographic image acquired by the radiographic device according to an embodiment of the present invention.

FIG. 5 is a diagram exemplarily showing an image of a radiographic image acquired by the radiographic device according to an embodiment of the present invention. As shown in FIG. 5, an X-ray image, which is the radiographic image, is displayed on the screen of the display unit 140. For reference, a horizontal axis and a vertical axis in FIG. 5 are coordinate axes for indicating pixel coordinates or image coordinates on the screen of the display unit 140. Accordingly, center coordinates of a center of the screen, that is, center coordinates of a center of the X-ray image, may be expressed as (512, 512).

The selection area setting process S120 is a process of setting the selection area by receiving the area selected in the radiographic image. Here, the selection area is an area selected in the X-ray image as shown in FIG. 5 according to a user's selection. When the display unit 140 is a touch screen, a user's hand or a touch pen may be used to set the selection area through a drag method. Alternatively, when an input unit such as a mouse is provided, the selection area may be set in a manner of starting to drag a mouse cursor at one point and ending the dragging at another point.

Figure 6:
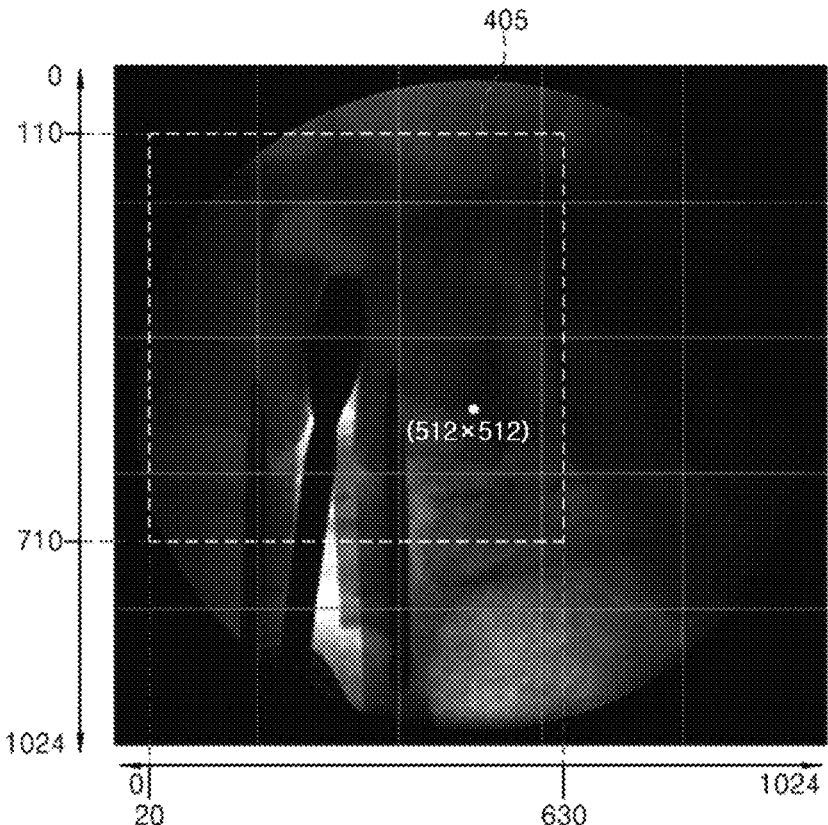
FIG. 6 is a schematic diagram showing an image showing a selection area in a radiographic image acquired by the radiographic device according to the present invention.
Figure 7:
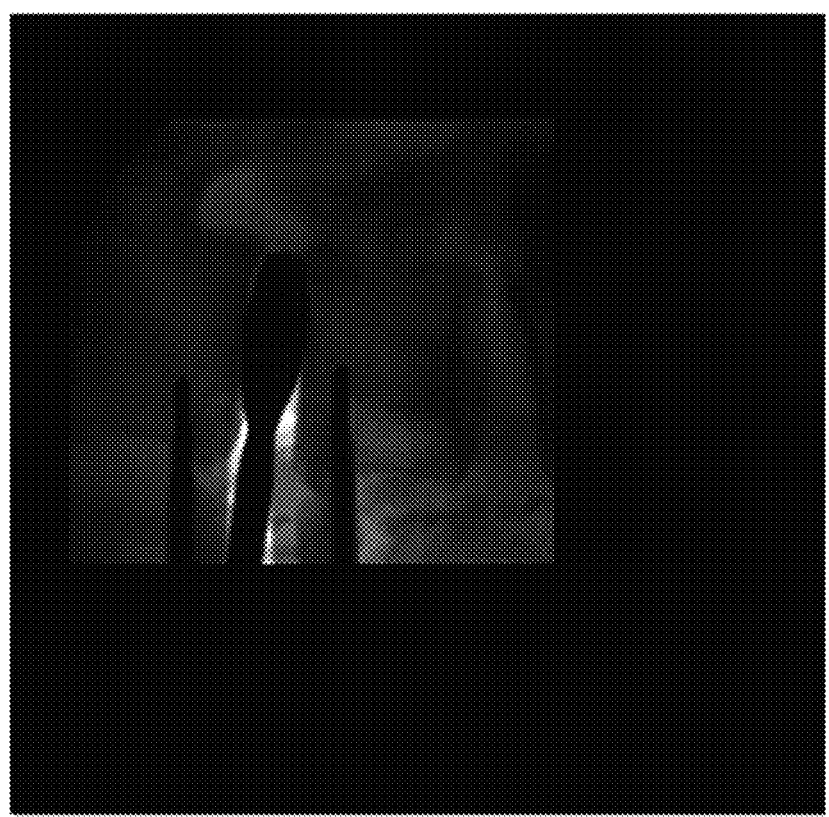
FIG. 7 is a schematic graph illustrating an image in which a portion other than a selection area is covered by the collimators in the radiographic device according to an embodiment of the present invention.

FIG. 6 is a schematic diagram showing an image showing a selection area in a radiographic image acquired by the radiographic device according to the present invention. For example, as shown in FIG. 6, when a user positions the user's hand, a touch pen, or a mouse cursor at coordinate points (20, 110) and starts dragging, and then ends the dragging at the coordinate points (630, 710), a quadrangular area connecting four coordinate points (20, 110), (20, 710), (630, 110), and (630, 710) is selected as a selection area 405. Here, the user may change and redesignate the selection area 405 or may determine the selection area 405. Redesignation for changing the selection area 405 may be performed in a manner of starting dragging at one point and ending the dragging at another point as described above. The selection area 405 may be determined without a separate input for determining the selection area, but as described above, the selection area 405 may be selected through dragging, and then a storage button (not shown) may be touched to determine the selection area 405. In this way, the selection area 405 may be set in the selection area setting process S120.

A user may input a target area, that is, an area to be enlarged, in a desired range, size, and shape through a touch gesture input such as dragging. In this case, a selection area selected by the user may be displayed on the display unit 140 (an area partitioned by a dotted line in FIG. 6). The user can easily confirm a selection area selected by the user on a displayed image through display of the selection area displayed by a user interface and can easily determine whether to determine the selection area displayed by his/her own manipulation or whether to reset the selection area. Accordingly, an unnecessary imaging process can be avoided to reduce radiation exposure.

A selection area may be set in various ways in addition to the above-described drag operation on the touch screen or a drag operation using a mouse. For example, a selection area may be set using various touch gesture input methods including a tap, a double tap, a press touch gesture, and the like.

In addition, setting, confirming, changing, resetting, and determining a selection area may be performed in various ways. For example, when the user taps and touches a specific point on an image displayed on the display unit 140, a basic selection area having a set size and a set shape such as a rectangular or circular shape on the screen may be displayed around a corresponding portion. Then, the displayed basic selection area may be touched and dragged to adjust a size and a shape and set an adjustment selection area, and then when a touch gesture for determining the adjustment selection area as a selection area, for example, a double tap touch, is input, the adjustment selection area may be set as a final selection area and maintained. Then, when the user inputs a touch gesture for capturing an image of the selection area, for example, a press touch within a certain time range, an image of the corresponding selection area may be captured. In this way, through various touch gesture inputs using the display unit 140 including the touch screen, a selection area may be set in various ways, and the collimator may be moved according to the selection area to control a radiation irradiation range, and an image may be captured.

The pixel coordinates or image coordinates (20, 110), (20, 710), (630, 110), and (630, 710) of the selection area selected by the user may be transmitted to the determination controller 130 and may be changed into coordinates of the collimator corresponding to the selection area 405 by the determination controller 130. The coordinates of the collimator corresponding to the selection area 405 are included in the above-described blocking information and transmitted to the radiation irradiator 110.

The collimator driving process S130 is a process of blocking the remaining portion excluding a portion of the flux of radiation corresponding to the selection area 405 using the collimator. As described above, the pixel coordinates or image coordinates (20, 110), (20, 710), (630, 110), and (630, 710) of the selection area selected by the user may be transmitted to the determination controller 130 and may be changed into the coordinates of the collimator corresponding to the selection area 405 by the determination controller 130.

The coordinates of the collimator corresponding to the selection area 405 are included in the above-described blocking information and transmitted to the radiation irradiator 110. Each of the four collimators 210, 220, 230, and

240 in the radiation irradiator 110 receiving the blocking information is moved as shown in FIG. 3 according to collimator coordinate information included in the blocking information, and a portion of the radiation flux 200 is blocked by the collimator. The unblocked radiation flux portion 205 corresponds to the selection area 405.

The four collimators 210, 220, 230, and 240 may each independently be moved and may be moved simultaneously. Therefore, it is possible to shorten a time taken for the four collimators 210, 220, 230, and 240 to move to block a portion of the radiation flux 200.

When the four collimators 210, 220, 230, and 240 are moved according to coordinate information of the collimator, a portion of the radiation flux 200, that is, a portion of an X-ray flux 200 is blocked when X-rays, which are radiation, are radiated, thereby reducing an exposure dose to a patient or user.

The second image display process S140 is a process of displaying the second radiographic image acquired by radiating the radiation flux portion 205 corresponding to the selection area 405 onto the irradiation target object.

That is, after the position movement of the four collimators is completed as described above, in the second image display process S140, X-rays are radiated on the irradiation target object, the X-rays penetrating the irradiation target object are received to acquire an image signal, and the second radiographic image, that is, a second X-ray image, is displayed on the screen based on the image signal such that a user or the like may confirm the acquired image signal.

That is, the radiation irradiator 110 radiates X-rays, which are radiation, onto the irradiation target object. When the radiation flux portion 205 corresponding to the selection area 405 is radiated from the radiation irradiator 110 to the irradiation target object, X-rays, which are radiation, penetrate a portion of the irradiation target object corresponding to the selection area 405 and are incident on the image acquisition unit 120. The image acquisition unit 120 acquires an image signal from incident X-rays and transmits the acquired image signal to the determination controller 130. The determination controller 130 transmits the image signal to the display unit 140, and the display unit 140 visually displays the second X-ray image, which is the second radiographic image, based on the image signal.

FIG. 6 is a schematic graph illustrating an image in which a portion other than a selection area is covered by four collimators in the radiographic device according to an embodiment of the present invention. As can be seen from FIG. 6, since an X-ray flux is blocked by the four collimators 210, 220, 230, and 240 at a portion other than the selection area 405, an image of a corresponding area is not displayed.

Here, since a portion corresponding to the selection area 405 is biased on the screen of the display unit 140, position control may be performed such that a center of the selection area 405 is positioned at a center of the screen of the display unit 140. That is, a position of an X-ray image of the selection area 405 may be adjusted such that center image coordinates (305, 300) of the selection area 405 are positioned at center coordinates (512, 512) of the screen. Position adjustment of the X-ray image of the selection area 405 may be performed through coordinate conversion.

Also, the selection area 405 of the second X-ray image may be enlarged and displayed to fill the screen of the display unit 140. The second X-ray image corresponding to the selection area may be image-fitted to the screen of the display unit 140 and displayed on the screen of the display unit 140. For example, the second X-ray image may be enlarged and fit to be displayed on the screen of the display unit 140.

Figure 8:
FIG. 8 is a schematic diagram showing an image showing an image of an enlarged and displayed selection area in a radiographic image acquired by the radiographic device according to the present invention.

FIG. 8 is a schematic diagram showing an image of an enlarged and displayed selection area on a second radiographic image acquired by the radiographic device according to the present invention. The selection area 405 on the second radiographic image may be enlarged and displayed as shown in FIG. 8. Enlarging and displaying the selection area 405 may be implemented in various forms. For example, a ratio of a length of the longest side in the selection area 405 to a length of the screen on which the X-ray image is displayed on the screen of the display unit 140 may be converted into a magnification ratio to enlarge the selection area 405. As described above, the selection area 405 in the second radiographic image may be enlarged and displayed as shown in FIG. 8.

As necessary, when the brightness of a radiographic image decreases or the sharpness of the radiographic image decreases as the selection area 405 is enlarged and displayed, the intensity of a radiation flux may be changed to complement the brightness of the radiographic image or the sharpness of the radiographic image.

The execution order of the processes S110, S120, S130, or S140 described above is not limited to the above-described order and may be changed as needed. In addition, each process may be repeatedly performed.

While the embodiments of the present invention have been described above, the scope of the present invention is not limited thereto, and various modifications and improved aspects made by those skilled in the art utilizing the basic concept of the present invention that are defined in the following claims also belong to the scope of the present invention.

DESCRIPTIONS OF REFERENCE NUMERALS

110: radiation irradiator
120: image acquisition unit
130: determination controller
140: display unit
200: flux of radiation
210, 220, 230, 240: collimator
405: selection area

The invention claimed is:

1. A radiographic device comprising:
an radiation irradiator configured to radiate radiation onto an irradiation target object and including a collimator configured to selectively block a flux of the radiation;
an image acquisition unit acquiring an image signal by receiving the radiation penetrating the irradiation target object;
a display unit displaying a radiographic image based on the image signal; and
a determination controller configured to control the radiation irradiator such that an irradiation range of the radiation corresponding to a selection area selected in the radiographic image is implemented,
wherein the display unit includes an input display which displays a first radiographic image for inputting the selection area and a main display which displays a second radiographic image captured and acquired under conditions corresponding to the selection area, wherein, for enlarging the selected area, the determination controller is further configured to:
acquire a plurality of image coordinates of the selection area for the first radiographic image based on the input display,
change the plurality of image coordinates into coordinates of the collimator corresponding to the selection area, and
transmit the coordinates of the collimator to the radiation irradiator,
wherein the radiation irradiator is further configured to move the plurality of collimators non-interlockingly or asymmetrically with each other, based on the coordinates of the collimator, to block at least a portion of the flux of the radiation,
wherein the image acquisition unit is further configured to acquire the second radiographic image by radiating the portion of the flux of the radiation corresponding to the selection area onto the irradiation target object,
wherein the main display is configured to display the second radiographic image by enlarging and fitting the second radiographic image to fill the main display, while displaying the first radiographic image on the input display, and
wherein, when brightness or sharpness of the second radiographic image decreases due to the enlargement of the second radiographic image, the radiation irradiator emits radiation according to a radiation output condition received from the determination controller to change intensity of a radiation flux to complement the brightness or the sharpness of the second radiographic image.

2. The radiographic device of claim 1, wherein the selection area is set with touch gesture input through the input display.

3. The radiographic device of claim 2, wherein the touch gesture includes at least one of a drag touch, a tap touch, a double tap touch, and a press touch.

4. The radiographic device of claim 2, wherein the selection area is set through a setting process including a process of setting a basic selection area with a first touch gesture, a process of changing the basic selection area with a second touch gesture to set a changed selection area, and a process of determining the changed selection area as the selection area with a third touch gesture.

5. A radiographic method comprising:
displaying a first radiographic image of an irradiation target object on an input display;
setting a plurality of image coordinates of a selection area by receiving an area selected in the radiographic image based on the input display;
changing the plurality of image coordinates into coordinates of a collimator corresponding to the selection area;
transmitting the coordinates of the collimator to a radiation irradiator;
radiating radiation having a radiation irradiation range corresponding to the selection area by at least partially blocking a flux of radiation by move the plurality of collimators non-interlockingly or asymmetrically with each other, based on the coordinates of the collimator;
acquiring a second radiographic image of the irradiation target object acquired by the radiated radiation corresponding to the selection area; and
displaying the second radiographic image by enlarging and fitting the second radiographic image to fill the main display, while displaying the first radiographic image on the input display, wherein, when brightness or sharpness of the second radiographic image decreases due to the enlargement of the second radiographic image, emitting, by the radiation irradiator, radiation according to a radiation output condition received from a determination controller to change intensity of a radiation flux to complement the brightness or the sharpness of the second radiographic image.

6. The radiographic method of claim 5, wherein, in the setting of the plurality of image coordinates of the selection area, the selection area is set with a touch gesture on the first radiographic image displayed on the input display.

* * * * *